(12) United States Patent
DeHaven et al.

(10) Patent No.: US 6,630,462 B2
(45) Date of Patent: Oct. 7, 2003

(54) DELTA AGONIST ANALGESICS

(75) Inventors: Robert DeHaven, Lansdale; Erin Gauntner, Phoenixville; Patrick Little, Media; Wei Y. Zhang, Collegeville, all of PA (US)

(73) Assignee: Adolor Corporation, Exton, PA (US)

( * ) Notice: Subject to any disclaimer, the term of this patent is extended or adjusted under 35 U.S.C. 154(b) by 0 days.

(21) Appl. No.: 10/059,953

(22) Filed: Nov. 16, 2001

(65) Prior Publication Data

US 2002/0156052 A1 Oct. 24, 2002

Related U.S. Application Data

(60) Provisional application No. 60/249,583, filed on Nov. 17, 2000.

(51) Int. Cl.⁷ .................. A61K 31/553; A61K 31/55
(52) U.S. Cl. .................. 514/211.13; 514/220
(58) Field of Search ................. 514/211.13, 220

(56) References Cited

U.S. PATENT DOCUMENTS

| | | | |
|---|---|---|---|
| 4,559,157 A | 12/1985 | Smith et al. | 252/90 |
| 4,608,392 A | 8/1986 | Jacquet et al. | 514/844 |
| 4,820,508 A | 4/1989 | Wortzman | 424/59 |
| 4,938,949 A | 7/1990 | Borch et al. | 424/10 |
| 4,992,478 A | 2/1991 | Geria | 514/782 |

FOREIGN PATENT DOCUMENTS

WO    WO 97/35584    10/1997

OTHER PUBLICATIONS

Jianquan, T., et al., "Analgesic and antipyretic effects of cyproheptadine," *Zhongguo Yaoli Xuebao*, 1990, 11(13), 204–207 (Abstract only).
Kobayashi, T. et al., "Effects of clozapine on the §–k–opioid receptors and the G–protein–activated K+ (GIRK) channel expressed in Xenopus oocytes" *British Journal of Pharmacology*, 1998, 123, 421–6.
Martindale, The Extra Pharmacopoeia, 28th ed. published 1982 by The Pharmaceutical Press, pg. 115.

*Primary Examiner*—Raymond Henley, III
(74) *Attorney, Agent, or Firm*—Woodcock Washburn LLP (57) ABSTRACT

Methods and pharmaceutical compositions for the treatment of pain, preferably with lowered risk of induction of seizure in a patient. The compositions contain active compounds that are tricyclic δ opioid receptor agonists of the general formula (I):

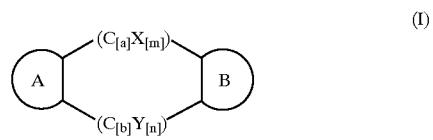

wherein rings A and B are aromatic rings of 5–7 carbons that are optionally substituted with one or more substituents that can include F, Cl, Br, I, $-NO_2$, $-OH$, $-SO_2$, or ($C_1-C_5$) alkyl; C is carbon, X, is N, O, S or P, and Y is N or P; [m] is an integer of 0 or 1, [a] is an integer of from 0 to 2, and the sum [m]+[a] is an integer of from 0 to 2; [n] is an integer of 0 to 1, [b] is an integer of 0 to 3, and the sum [n]+[b] is an integer of from 1 to 3; the sum [m]+[a]+[n]+[b] is an integer of from 1 to 3; and one $C_{[b]}$ or one $Y_{[n]}$ has a pendant substituted or unsubstituted piperidine or piperazine ring.

5 Claims, 6 Drawing Sheets

N-desmethylclozapine is a full agonist at the human δ opioid receptor

- BW373U86 (EC$_{50}$ = .46 nM)
- SNC-80 (EC$_{50}$ = 15 nM)
- DMCLZ (EC$_{50}$ = 290 nM)

N-desmethylclozapine is antinociceptive in acetic acid-induced writhing in mice

FIG. 6

DELTA AGONIST ANALGESICS

CROSS REFERENCE TO RELATED APPLICATIONS

This application claims priority of U.S. Provisional Patent Application No. 60/249,583, filed on Nov. 17, 2000, the disclosure of which is hereby incorporated herein by reference in its entirety, as if fully set forth herein.

FIELD OF THE INVENTION

The present invention relates to δ receptor agonist compounds and their use in the treatment of pain. Specifically, tricyclic δ receptor agonist compounds are disclosed, which have a tricyclic structure comprising a non-aromatic central ring flanked by two aromatic rings, and an optional pendant, substituted, piperazine or piperidine, together with their methods of use for the treatment of pain with reduced risk of induction of seizure in a patient.

BACKGROUND OF THE INVENTION

Clozapine (CLZ, 8-chloro-11-(4-methyl-1-piperazinyl)-5H-dibenzo[b,e][1,4]-diazepine) is an atypical antipsychotic or neuroleptic agent that is a dibenzodiazepine derivative with a piperazinyl side chain. It displays antipsychotic efficacy against positive and negative symptoms of schizophrenia in patients who do not respond to typical neuroleptics. It is metabolized via the hepatic microsomal enzyme system into two major metabolites: N-desmethylclozapine (DMCLZ) and clozapine N-oxide. DMCLZ has been shown to reach a plasma level of ~620 nM in human patients and is a potent 5HT1C receptor antagonist.

Clozapine inhibits binding at δ opioid receptors (Kobayashi, T., Ikeda, K. & Kumanishi, T. (1998) Br. J. Pharmacol. 123:421–6). Clozapine also acts as a kappa agonist and as a G-protein-activated inwardly rectifying K+ (GIRK) channel blocker. However, clozapine and other atypical antipsychotic agents frequently possess untoward side-effects, including induction of seizures. There is therefore a need, within the field of opioid receptor agonists, for compounds that are agonists of specific subtypes of opioid receptor that exhibit improved specificity and do not cause seizures.

The present invention addresses the aforementioned problems and more as will be apparent to one of skill in the art upon reading the following disclosure.

SUMMARY OF THE INVENTION

The present invention, in its broadest aspect, encompasses the use of δ receptor agonist compounds for the treatment of pain, wherein the δ receptor agonist compounds have a tricyclic structure comprising a non-aromatic central ring flanked by two or three aromatic rings, and an optional pendant, substituted, piperazine or piperidine.

In one embodiment, the invention therefore comprises the inducement of analgesia in a patient, where the methods comprise administering to a patient a δ opioid receptor agonist of the general formula (I):

(I)

wherein:
  rings A and B are aromatic rings of 5–7 carbons that are optionally substituted with one or more substituents that can include F, Cl, Br, I, —NO₂, —OH, —SO₂, or (C₁–C₅)alkyl;
  C is carbon, X is N, O, S or P, and Y is N or P;
  [m] is an integer of 0 or 1, [a] is an integer of from 0 to 2, and the sum [m]+[a] is an integer of from 0 to 2;
  [n] is an integer of 0 to 1, [b] is an integer of 0 to 3, and the sum [n]+[b] is an integer of from 1 to 3;
  the sum [m]+[a]+[n]+[b] is an integer of from 1 to 3; and
  one $C_{[b]}$ or one $Y_{[n]}$ has a pendant substituted or unsubstituted piperidine or piperazine ring.

Another aspect of the invention relates to methods of inducing analgesia in a patient, wherein the methods comprise administering to said patient an effective amount of a tricyclic δ opioid receptor agonist of the formula (Ia):

(Ia)

wherein:
  X are each independently 0–4 substituents independently selected from the group consisting of F, Cl, Br, I, —NO₂, —OH, —SO₂, and (C₁–C₅)alkyl;
  R₁ is C, N, O or S;
  R₂ is C or N; and
  R₃ is —H or —CH₃.

Still another aspect of the invention relates to methods of inducing analgesia in a patient, wherein the methods comprise administering to said patient an effective amount of a tricyclic δ opioid receptor agonist of the formula (Ib):

(Ib)

wherein:
  X is F, Cl, Br, or I;
  R₁ is C, N, O or S; and
  R₃ is —H or —CH₃.

Yet another aspect of the invention relates to methods of inducing analgesia in a patient, wherein the methods comprise administering to the patient an effective amount of a tricyclic δ opioid receptor agonist of the formula (Ic):

(Ic)

wherein R is —H or methyl, with —H being preferred.

Still another aspect of the invention relates to methods of inducing analgesia in a patient, said method comprising administering to said patient an effective amount of a compound selected from the group consisting of N-desmethylclozapine, amoxapine, cyproheptadine, and mixtures thereof.

Still another aspect of the invention relates to methods of inducing analgesia in a patient, wherein the methods comprise administering to said patient an effective amount of a tricyclic δ opioid receptor agonist of the formula (II):

(II)

wherein:
$R_4$ and $R_5$ are independently selected from alkyl, halo, haloalkyl, thio or alkoxy;
$R_6$ is C, N, O or S;
$R_7$ is C or N; and
$R_8$ is —H or —CH$_3$.

These and other aspects of the invention will become more apparent from the following detailed description.

DESCRIPTION OF THE PREFERRED EMBODIMENTS

As employed above and throughout the disclosure, the following terms, unless otherwise indicated, shall be understood to have the following meanings.

"Alkyl" refers to an aliphatic hydrocarbon group which may be straight, branched or cyclic having from 1 to about 10 carbon atoms in the chain, and all combinations and subcombinations of ranges therein. In certain preferred embodiments, the alkyl group is a $C_1$–$C_5$ alkyl group, i.e., a branched or linear alkyl group having from 1 to about 5 carbons. Exemplary alkyl groups include methyl, ethyl, n-propyl, isopropyl, butyl, isobutyl, sec-butyl, tert-butyl, pentyl, hexyl, heptyl, octyl, nonyl and decyl.

"Alkoxy" refers to an alkyl-O- group where alkyl is as previously described. Exemplary alkoxy groups include, for example, methoxy, ethoxy, propoxy, butoxy and heptoxy.

"Halo" refers to fluoro, chloro, bromo or iodo.

"Haloalkyl" refers to an alkyl group substituted with a halogen atom.

"Effective amount" refers to an amount of a compound as described herein that may be therapeutically effective to prevent or treat the symptoms of particular disorder. Such disorders include, but are not limited to, painful disorders, wherein the treatment or prevention comprises, for example, inhibiting the activity thereof by contacting cells, tissues and/or receptors with compounds as described herein.

The present invention, in its broadest aspect, encompasses the use of compounds for the treatment of pain, wherein the compounds have a tricyclic structure comprising a non-aromatic central ring flanked by two or three aromatic rings, and an optional pendant, substituted, piperazine or piperidine. In preferred form, the compounds employed in the methods of the present invention, as discussed in detail herein, are agonists of the δ opioid receptor, and are preferably substantially devoid of seizure inducing activity. The term "substantially devoid of seizure inducing activity", as used herein, means that less than about 20% of the pharmacological activity of the active compounds employed in the present methods results in the induction of seizures. In preferred embodiments, the compounds employed in the present methods exhibit less than about 15% of their pharmacological activity in the form of seizure induction, with less than about 10% being more preferred. In even more preferred embodiments, the present compounds exhibit less than about 5% of their pharmacological activity in the form of seizure induction, with about 0% (i.e., no inducement of seizures) being still more preferred.

Broadly speaking, the present invention is directed to methods for the treatment of pain. The methods of the present invention generally comprise administering to a patient a δ opioid receptor agonist to thereby induce analgesia in the patient. In one embodiment, the analgesia inducing methods of the present invention comprise administering to a patient a δ opioid receptor agonist of the general formula (I):

(I)

wherein:
rings A and B are aromatic rings of 5–7 carbons that are optionally substituted with one or more substituents that can include F, Cl, Br, I, —NO$_2$, —OH, —SO$_2$, or (C$_1$–C$_5$)alkyl;
C is carbon, X is N, O, S or P, and Y is N or P;
[m] is an integer of 0 or 1, [a] is an integer of from 0 to 2, and the sum [m]+[a] is an integer of from 0 to 2;

[n] is an integer of 0 to 1, [b] is an integer of 0 to 3, and the sum [n]+[b] is an integer of from 1 to 3;

the sum [m]+[a]+[n]+[b] is an integer of from 1 to 3; and one $C_{[b]}$ or one $Y_{[n]}$ has a pendant substituted or unsubstituted piperidine or piperazine ring.

In accordance with the present embodiment, the central non-aromatic ring has from about 5 to about 7 members, where up to one of the carbon atoms of the ring in each of the bridging regions can be substituted (i.e., replaced) by a heteroatom such as N, O, S or P. Preferably, the central non-aromatic ring has about 6 to about 7 members. Furthermore, in this embodiment, one $C_{[b]}$ or one $Y_{[n]}$ has a pendant substituted or unsubstituted piperidine or piperazine ring. In further embodiments of this general structure, unsubstituted piperidine or piperazine substituents are preferred.

As would be apparent to one of ordinary skill in the art, once armed with the teachings of the present disclosure, the particular degree of saturation or unsaturation of $C_{[a]}$, $C_{[b]}$, $X_{[m]}$ and $Y_{[n]}$ in the compounds of formula (I) may vary, and all forms are intended to be within the scope of the compounds of formula (I). In this regard, $X_{[m]}$ may be, for example, =N— or —NH—, and $C_{[a]}$ may be, for example, —CH— or —CH$_2$—. Thus, for example, when $X_{[m]}$ is =N— and [a] and [m] are 1, then $C_{[a]}$ is —CH—. When $X_{[m]}$ is —NH— and [a] and [m] are 1, then $C_{[a]}$ is —CH$_2$—.

Similarly, $Y_{[n]}$ may be, for example, =N—, —NH— or —N(Q)—(where Q is the pendant piperidine or piperazine ring) and $C_{[b]}$ may be, for example, —CH—, —CH$_2$—, —CH(Q)—, =C(Q) or —C(=Q)—(where Q is the pendant piperidine or piperazine ring). Thus, for example, when $Y_{[n]}$ is =N—, [b] and [n] are 1, and the pendant piperidine or piperazine ring is attached to $C_{[b]}$, then $C_{[b]}$ is —C(Q)—. When $Y_{[n]}$ is —NH—, [b] and [n] are 1, and the pendant piperidine or piperazine ring is attached to $C_{[b]}$, then $C_{[b]}$ is —CH(Q)— or —C(=Q)—. When $Y_{[n]}$ is —N(Q)—, and [b] and [n] are 1, then $C_{[b]}$ is —CH$_2$—.

In another embodiment, the analgesia inducing methods of the present invention comprise administering to a patient a δ opioid receptor agonist of the general formula (Ia):

wherein:
X are each independently 0–4 substituents independently selected from the group consisting of F, Cl, Br, I, —NO$_2$, —OH, —SO$_2$, and (C$_1$–C$_5$)alkyl;

$R_1$ is C, N, O or S;

$R_2$ is C or N; and $R_3$ is —H or —CH$_3$.

As would be apparent to one of ordinary skill in the art, once armed with the teachings of the present disclosure, the definitions C and N in $R_1$ in formula (Ia) are intended to refer to —CH$_2$— and —NH—, respectively. Similarly, the definitions C and N in $R_2$ in formula (Ia) are intended to refer to —CH$_2$— and —NH—, respectively.

In still another embodiment, the analgesia inducing methods of the present invention comprise administering to a patient a δ opioid receptor agonist of the general formula (Ib):

wherein:
X is F, Cl, Br, or I;

$R_1$, is C, N, O or S; and $R_3$ is —H or —CH$_3$.

As with formula (Ia) above, and as would be apparent to one of ordinary skill in the art, once armed with the teachings of the present disclosure, the definitions C and N in $R_1$ in formula (Ib) are intended to refer to —CH$_2$— and —NH—, respectively.

In yet another embodiment, the analgesia inducing methods of the present invention comprise administering to a patient a δ opioid receptor agonist of the general formula (Ic):

wherein R is —H or methyl, with —H being preferred.

In still another embodiment, the analgesia inducing methods of the present invention comprise administering to a patient a δ opioid receptor agonist of the general formula (II):

wherein:
$R_4$ and $R_5$ are independently selected from alkyl, halo, haloalkyl, thio or alkoxy;

$R_6$ is C, N, O or S;

$R_7$ is C or N; and $R_8$ is —H or —CH$_3$.

As with formulas (I) and (Ia) above, and as would be apparent to one of ordinary skill in the art, once armed with the teachings of the present disclosure, the definitions C and N in $R_6$ in formula (II) are intended to refer to —$CH_2$— and —NH—, respectively. Similarly, the definitions C and N in $R_7$ in formula (II) are intended to refer to —CH— and —N—, respectively.

In yet another embodiment, the analgesia inducing methods of the present invention comprise administering to a patient an effective amount of a compound selected from the group consisting of N-desmethylclozapine, amoxapine, cyproheptadine, and mixtures thereof.

In accordance with the present invention, the δ opioid agonists, N-desmethyl analogs of clozapine and loxapine (i.e., DMCLZ and amoxapine, respectively) constitute preferred embodiments of the present invention, but as is apparent, for example, from general formula (I), phenothiazines, thioxanthenes, and related tricyclic compounds may also have δ opioid receptor agonist activity, and therefore fall within the scope of the present invention.

The compounds of the present invention include all hydrates and salts that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a patient, such as a human patient, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be from about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected are using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), the disclosures of which are hereby incorporated herein by reference, in their entireties.

Useful dosages of the compounds of the present invention can be determined by comparing their in vitro activity, and in vivo activity in animal modes. Methods for the extrapolation of effective dosages in mice, and other animals, to humans are known to the art; for example, see U.S. Pat. No. 4,938,949, the disclosure of which is hereby incorporated herein by reference, in its entirety.

Generally, the concentration of the active compound(s), for example, the compounds of formulas (I), (II), (III) and (IV), in a liquid composition, such as a lotion, will be from about 0.1 to about 25 wt %, preferably from about 0.5 to about 10 wt %. The concentration in a semi-solid or solid composition such as a gel or a powder will be from about 0.1 to about 5 wt %, preferably from about 0.5 to about 2.5 wt %. Single dosages for injection, infusion or ingestion will generally vary from about 5 to about 1500 mg, and may be administered, e.g., 1–3 times daily, to yield levels of about 0.1 to about 50 mg/kg, for adults. A preferred dosage of the present invention is from about 7.5 to about 45 mg per day, administered orally, with appropriate adjustment for the body weight of an individual.

Accordingly, the invention includes a pharmaceutical composition comprising a compound of the present invention as described above; or a pharmaceutically acceptable salt thereof, in combination with a pharmaceutically acceptable carrier. Pharmaceutical compositions adapted for oral, topical or parenteral administration, comprising an amount of one or more compounds effective to treat pain, are a preferred embodiment of the invention. The present invention will be fully understood by one of skill in the art by reference to the following embodiments, examples, and claims.

EXAMPLES

N-Desmethylclozapine is a Potent δ Opioid Receptor Agonist

In Vitro Methods:

Preparation of Membranes:

Chinese hamster ovary (CHO) cells are stably transfected with the cloned human μ, κ, or δ opioid receptors. Cells are harvested by scraping them from the culture flask, centrifuging them at 1000×g for 10 min, resuspending them in buffer A and centrifuging again to remove growth medium. The cells are resuspended again in buffer A and homogenized for 30 seconds using a Polytron homogenizer (Brinkmann) at setting 8. The homogenate is centrifuged at 48,000×g for 10 min at 4° C. The pellets are resuspended at 1 mg of protein per mL of buffer A and aliquots stored at −80° C. until use. Buffer A is 50 mM Tris HCl, pH 7.8, containing 1.0 mM EGTA, 5 mM MgC12, 10 mg/mL leupeptin, 10 mg/mL pepstatin A, 200 mg/mL bacitracin, and 0.5 mg/mL aprotinin.

Opioid Receptor Binding Assays:

Receptor binding assays contain 0.4–1.0 nM [3H] diprenorphine (~40,000 dpm), test compound as appropriate, and membrane preparation in a total volume of 0.5 mL buffer A. After incubation at room temperature for one hour, the samples are filtered through Whatman GF/B filters that have been presoaked in a solution of 0.5% (w/v) polyethylenimine and 0.1% (w/v) bovine serum albumin in water. The filters are rinsed 4×1 mL with cold 50 mM Tris HCl, pH 7.8 and radioactivity remaining on the filters is determined by scintillation spectroscopy. Ki values are determined by Cheng-Prusoff corrections of IC50 values derived from nonlinear regression fits of 12 point titration curves using the program Prism© (GraphPad Software, San Diego, Calif.).

Opioid Receptor-mediated Stimulation of [35S]GTPγS Binding:

Assays contain 80–100 pM [35S]GTPγS, 3.0 mM GDP, 75 mM NaCl, 15 mM $MgCl_2$, 1.0 mM EGTA, 2.1 mM dithiothreitol, 10 mg/mL leupeptin, 10 mg/mL pepstatin A, 200 mg/mL bacitracin, 0.5 mg/mL aprotinin, 50–100 mg of membrane protein and agonist as appropriate in a final total volume of 250 mL of 50 mM Tris HCl, pH 7.8 in 96 well Basic Flashplates® (NEN). After incubation for one hour at room temperature, the samples are centrifuged at 800×g at 4° C. for 5 min and the radioactivity (cpm) bound to the membranes is determined by scintillation spectrometry.

To determine the $IC_{50}$ value, which is the concentration to give half-maximal inhibition of agonist-stimulated [35S] GTPγS binding, the cpm of [35S]GTPγS bound in the presence of a fixed concentration of agonist and various concentrations of antagonist is measured. The fixed concentration of agonist is the EC80 for the agonist, which is the concentration to give 80% of the relative maximum stimulation of [35S]GTPγS binding. The $IC_{50}$ value is determined from a best nonlinear regression fit of the data which is performed using the program Prism®.

In Vivo Methods:

Formalin-induced Flinching:

Male Sprague-Dawley rats weighing 80–120 g are injected s.c. with 50 ml of a 5% formalin solution into the dorsal surface of the right hind paw (i.paw). The flinching behavior is quantified by counting the number of responses that occur during the tonic (late) phase of pain, lasting from 20–35 min after formalin injection. The test compounds are injected i.paw 10 min prior to the formalin injection. The mean percent antagonism (%A) of formalin-induced flinching for drug treated, formalin injected rats is calculated according to the following formula:

%A=(Mean formalin response−Mean saline response)−Individual response×100/Mean formalin response−Mean saline response The mean formalin response is the mean number of flinches in rats treated with vehicle prior to the formalin injection. The mean saline response is the mean number of flinches in rats treated with 50 ml saline instead of formalin.

Acetic Acid-induced Writhing:

Male ICR mice weighing 20–25 g are injected s.c. with either vehicle or test compound 15 min before they are injected intraperitoneally with 0.6% acetic acid. At 5 min after treatment with acetic acid, the number of writhes is counted for 10 min. Dose response curves are expressed as the percent inhibition of acetic acid induced writhing, when compared to the mean number of writhes observed in vehicle-treated mice.

The mean percent inhibition (%I) of acetic acid-induced writhing for drug-treated rats is calculated according to the following formula:

$$\% \ I = \frac{(\text{Mean vehicle response} - \text{Mean individual response}) \times 100}{\text{Mean vehicle response}}$$

The mean individual response is the mean number of writhes in rats treated with test compound. The mean vehicle response is the mean number of writhes in rats treated with vehicle.

Drug-Induced Seizures:

Mice are injected s.c. with either vehicle (1:1:8, DMSO: Cremophor: Saline), clozapine (3–30 mg/kg), or DMCLZ (3–30 mg/kg). Immediately after injection, the mice are placed in individual plastic cages (30×16×12 cm) lined with bedding. The mice are observed for gross behavioral signs for 30 min, and the presence or absence of seizures is noted.

To determine the role of δ opioid receptors in mediating clozapine-induced seizures, mice are pretreated with either saline or the selective δ antagonist naltrindole (NTI) (1 mg/kg, s.c.) 20 min prior to treatment with vehicle or 30 mg/kg of clozapine.

RESULTS

It is demonstrated herein, with reference to FIGS. 2–7, that DMCLZ is a potent and selective δ opioid receptor agonist with antinociceptive properties. Amoxapine, a structurally related desmethyl metabolite of another antipsychotic agent, loxapine, also inhibits δ opioid receptor binding.

It is further shown that, in contrast to other δ opioid agonists with similar structures, DMCLZ does not produce seizures in mice and therefore is a useful compound δ opioid receptor agonist.

Figure 2:
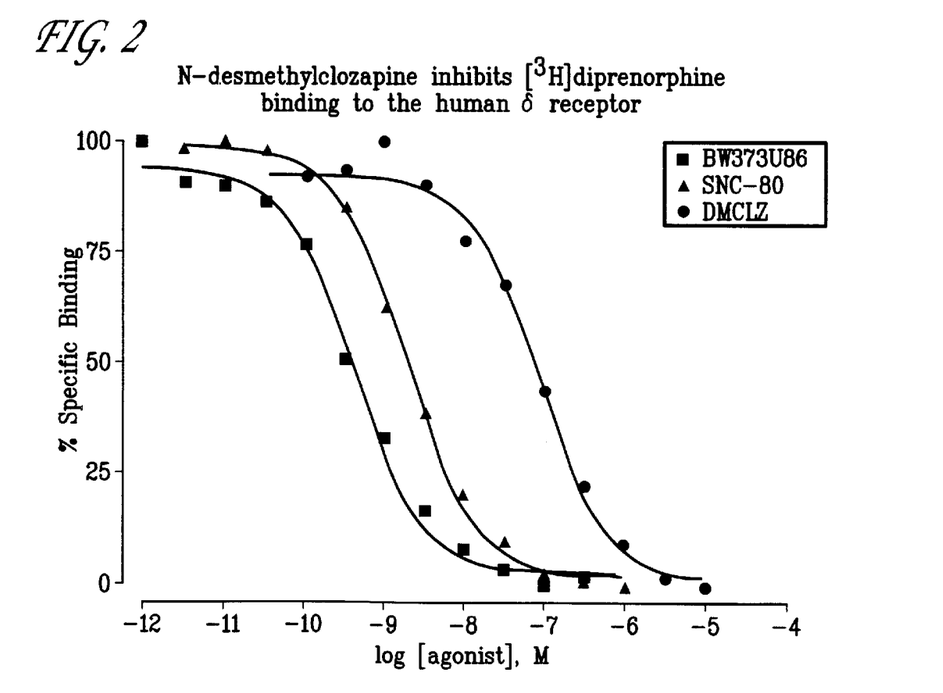
FIG. 2 shows that N-desmethylclozapine inhibits tritiated-diprenorphine binding to the human δ opioid receptor.
Figure 3:
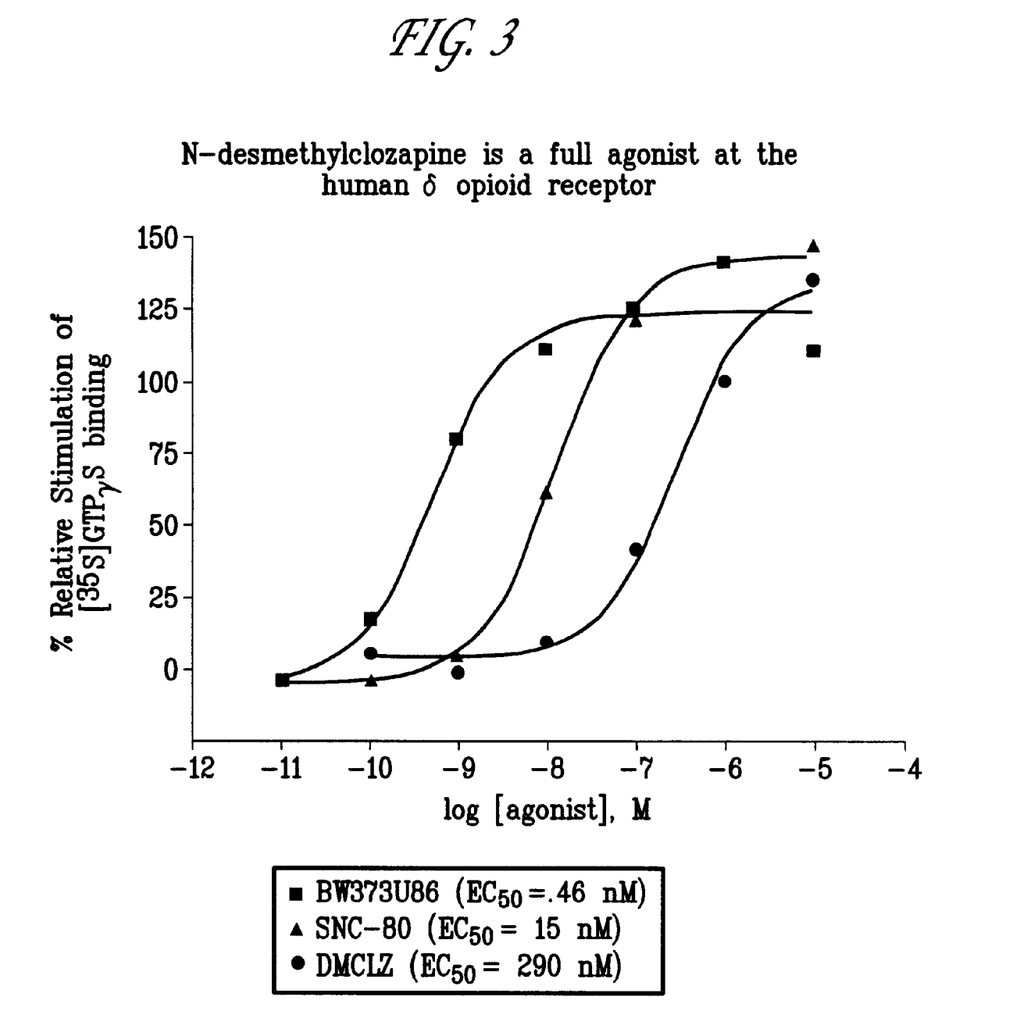
FIG. 3 shows that N-desmethylclozapine is a full agonist of the human δ opioid receptor.

With reference to FIGS. 2 and 3 it is shown that N-desmethylclozapine (DMCLZ) is a potent and selective δ opioid receptor agonist with a Ki of 24 nM at the cloned human δ receptor and an EC50 of 290 nM in δ receptor mediated stimulation of [35S]GTPγS binding, respectively.

Figure 4:
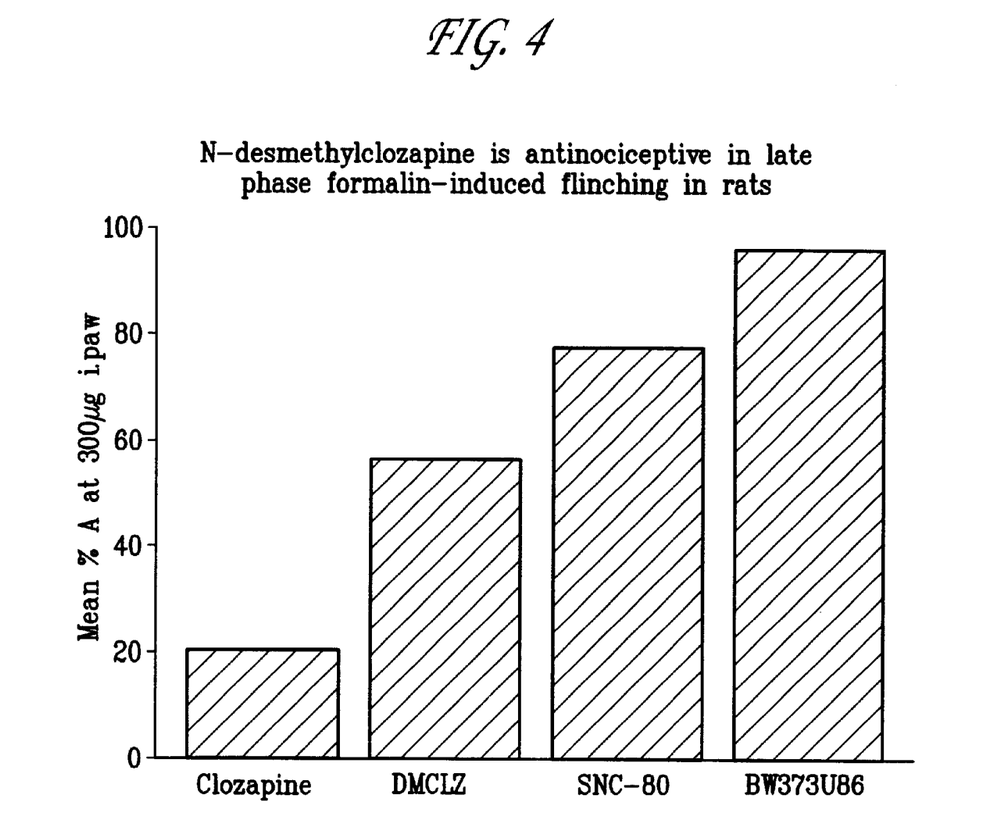
FIG. 4 shows that N-desmethylclozapine is antinociceptive in late phase formalin-induced flinching in rats.

With reference now to FIG. 4, it is shown that DMCLZ is antinociceptive in the formalin-induced flinching model in the rat, producing 56% A at a dose of 300 μg i.paw.

Figure 5:
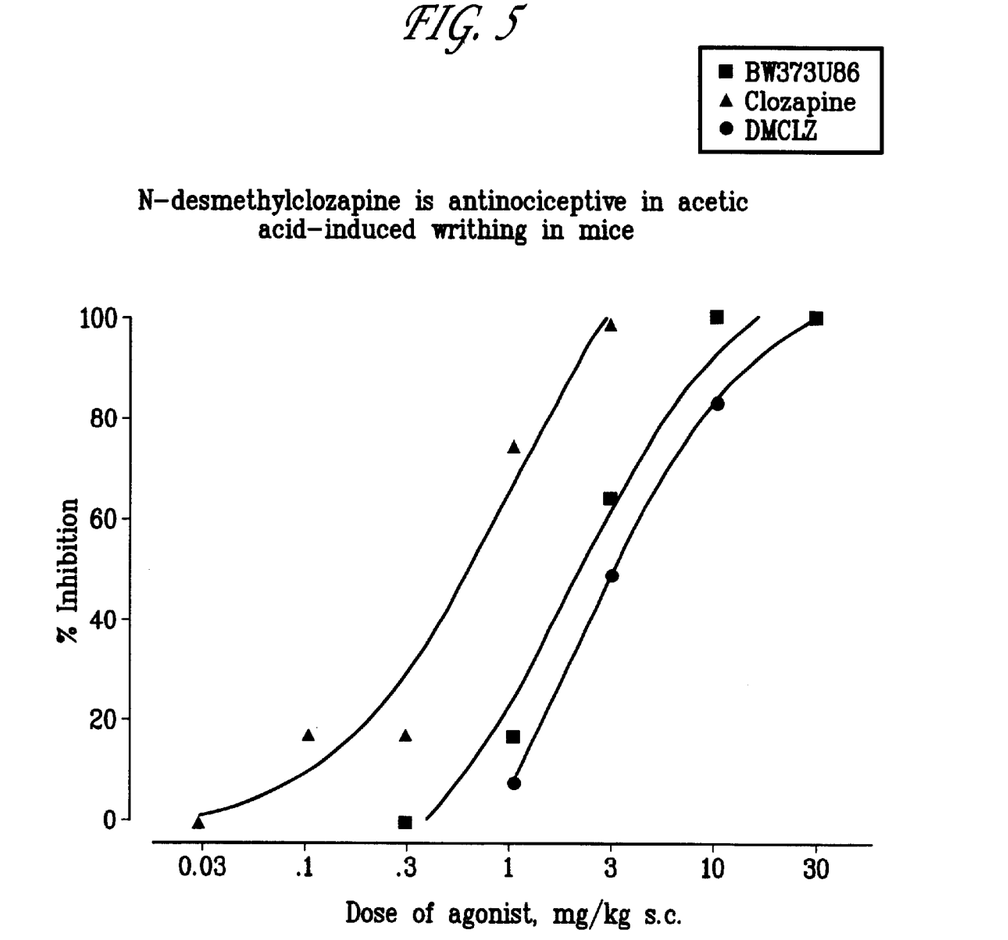
FIG. 5 shows that N-desmethylclozapine is antinociceptive in acetic acid-induced writhing in mice.

With reference now to FIG. 5, it is shown that DMCLZ is antinociceptive in the acetic acid-induced writhing model in the mouse, with an ED50 of 2.2 mg/kg s.c.

Figure 6:
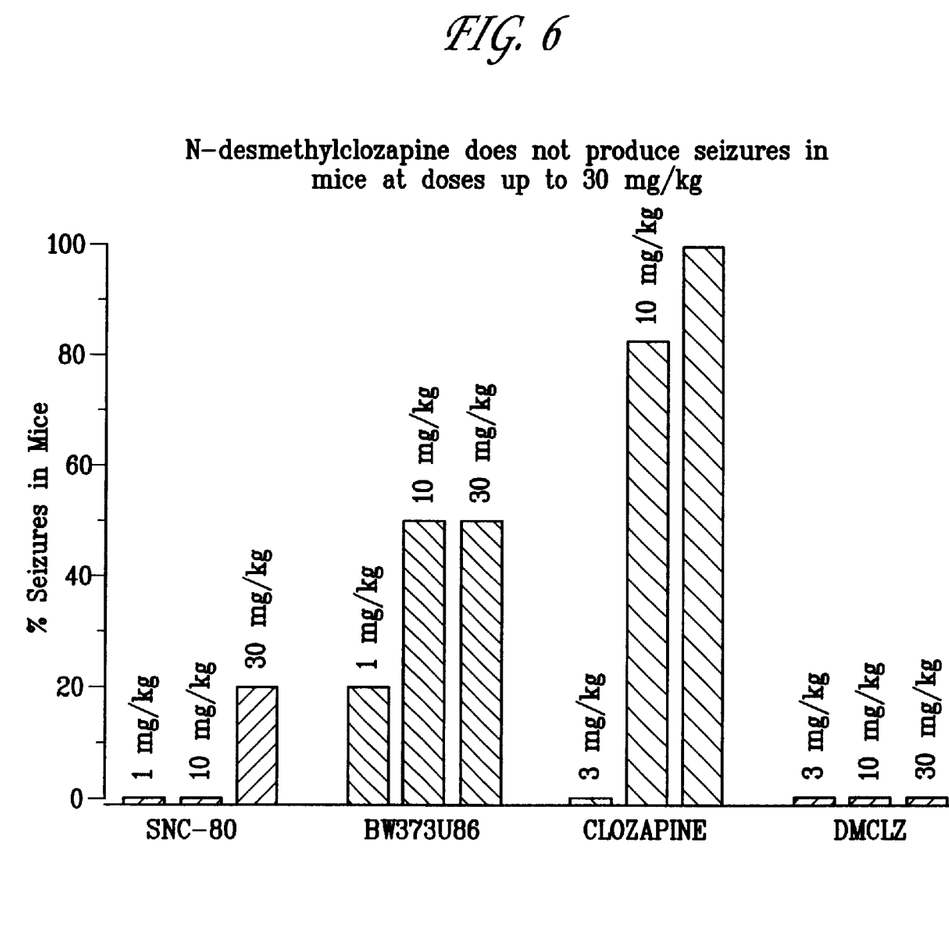
FIG. 6 shows that N-desmethylclozapine does not induce seizures in mice at dosages of up to 30 mg/kg.

With reference now to FIG. 6, it is shown that DMCLZ does not produce seizures in mice at doses up to 30 mg/kg, in contrast to clozapine (CLZ) and the δ opioid agonists BW373U86 and SNC-80.

Figure 7:
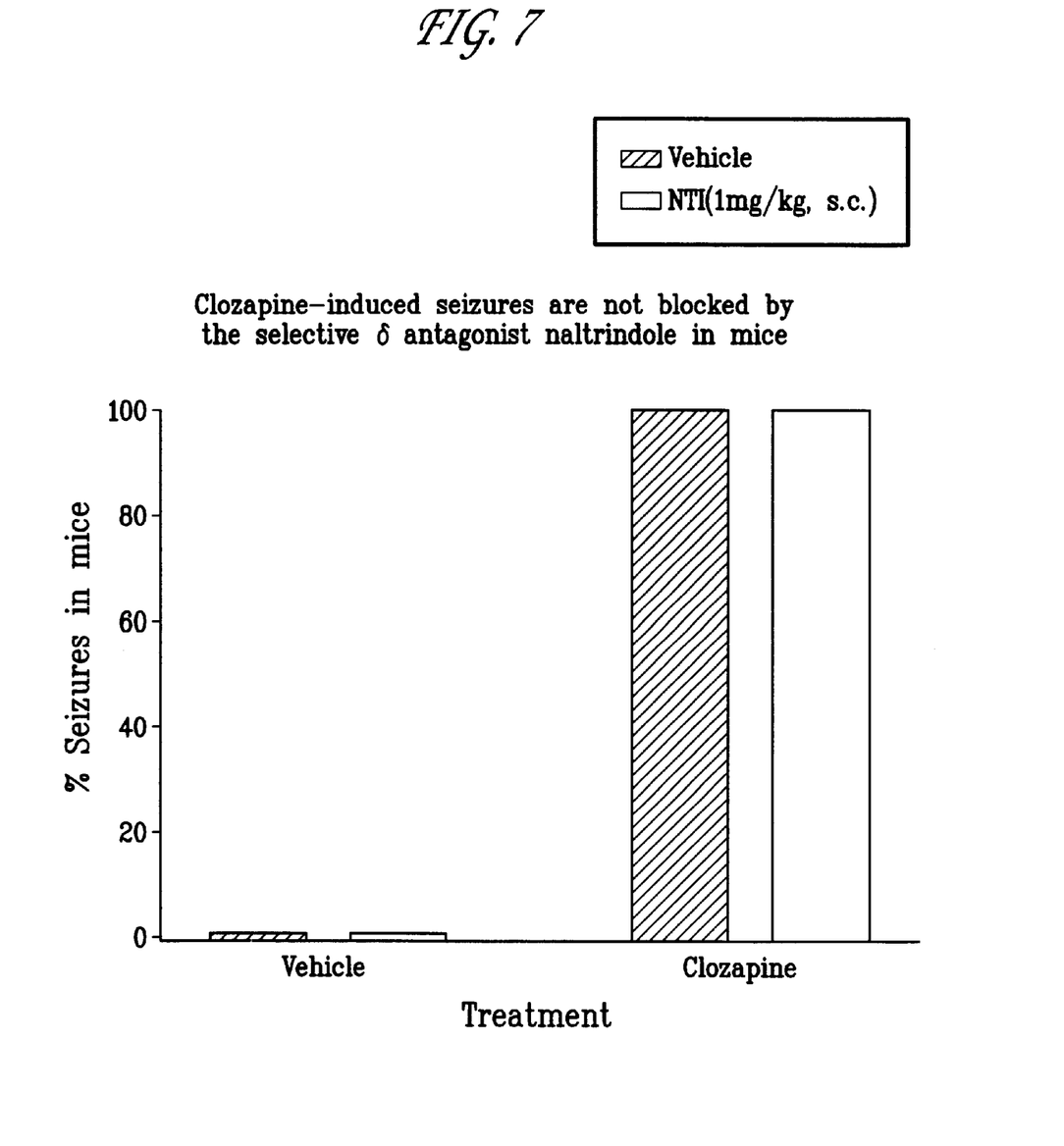
FIG. 7 shows that clozapine-induced seizures are not blocked by the selective δ antagonist naltrindole in mice.

Finally, with reference to FIG. 7, it is shown that clozapine-induced seizures in mice are not mediated by the δ opioid receptor, since they are not blocked by the selective δ antagonist naltrinidole.

Therefore, the foregoing results collectively show that DMCLZ is a δ opioid receptor agonist with reduced side effects.

Figure 1:
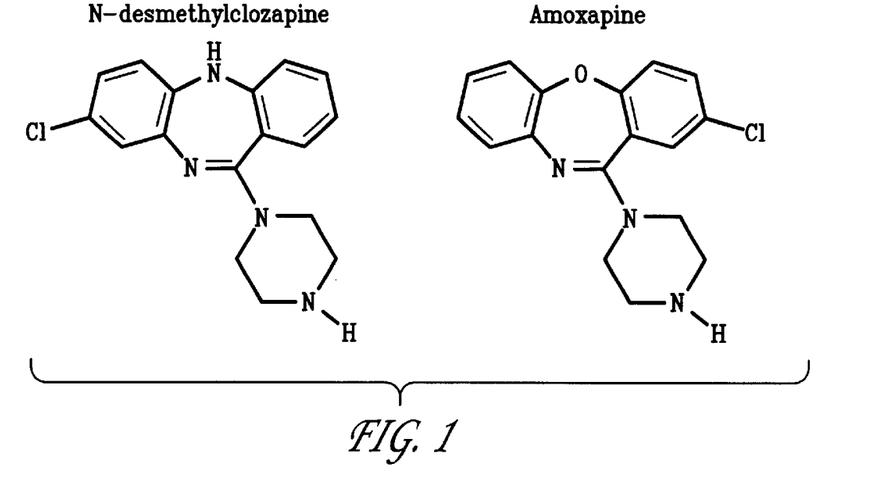
FIG. 1 shows the structure of two embodiments of the compounds useful in the present invention, N-desmethylclozapine and amoxapine.

It is further shown that structurally related compounds such as amoxapine (FIG. 1), which is a structurally related desmethyl metabolite of another antipsychotic agent, loxapine, also inhibits δ opioid receptor binding, as shown in TABLE I.

TABLE I

N-desmethylclozapine is a potent, selective inhibitor of [³H]dinprenorphine binding to the human δ opioid receptor

| | K$_i$(nM) or % Inhibition @ 10 μM | | |
|---|---|---|---|
| Compound | δ | κ | μ |
| N-desmethylclozapine | 24 | 64% | 17% |
| Clozapine | 928 | 11% | 17% |
| Amoxapine | 279 | 25% | 18% |
| Loxapine | 26% | 27% | 0% |
| BW373U86 | 0.075 | 149 | 96 |
| SNC-80 | 0.47 | 2% @ 1.0 μM | 5.5% |

Comparison of the structures of the δ opioid agonists shown in TABLE I reveal common structural features of δ opioid agonists. Thus, N-desmethyl analogs of clozapine and loxapine constitute preferred embodiments of the present invention, but formula (I) set forth herein indicates that phenothiazines, thioxanthenes, and related tricyclic structures also have δ opioid receptor agonist activity, and also fall within the scope of the present invention.

The disclosures of each patent, patent application and publication cited or described in this document are hereby incorporated herein by reference, in their respective entireties.

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

What is claimed is:

1. A method of inducing analgesia in a patient, said method comprising administering to a patient a δ opioid receptor agonist of the general formula (I):

wherein:

rings A and B are aromatic rings of 5–7 carbons that are optionally substituted with one or more substituents that can include F, Cl, Br, I, —NO$_2$, —OH, —SO$_2$, or (C$_1$–C$_5$)alkyl;

C is carbon, X, is N, O, S or P, and Y is N or P;

[m] is an integer of 0 or 1, [a] is an integer of from 0 to 2, and the sum [m]+[a] is an integer of from 0 to 2;

[n] is an integer of 0 to 1, [b] is an integer of 0 to 3, and the sum [n]+[b] is an integer of from 1 to 3;

the sum [m]+[a]+[n]+[b] is an integer of from 1 to 3; and one C$_{[b]}$ or one Y$_{[n]}$ has a pendant substituted or unsubstituted piperidine or piperazine ring;

with the provisos that when rings A and B are each phenyl, [a] is 2 and [m] is 0 such that bridging region (C$_{[a]}$X$_{[m]}$) is (CH=CH), [b] is 1 and [n] is 0, then C$_{[b]}$ has a pendent substituted or unsubstituted piperazine ring, and when ring A is phenyl, ring B is chlorophenyl, X is N, [a] is 0, [m] is 1, and Y is N, [b] is 1 and [n] is 1 such that bridging region ($C_{[b]}Y_{[n]}$) is (CH=N), then $C_{[b]}$ had a pendent substituted or unsubstituted piperidine ring.

2. A method of inducing analgesia in a patient, said method comprising administering to said patient an effective amount of a tricyclic δ opioid receptor agonist of the formula (Ia):

(Ia)

wherein:

X are each independently 0–4 substituents independently selected from the group consisting of F, Cl, Br, I, $-NO_2$, $-OH$, $-SO_2$, and ($C_1-C_5$)alkyl;

$R_1$ is C, N, O or S;

$R_2$ is C or N; and $R_3$ is $-H$ or $-CH_3$.

3. A method of inducing analgesia in a patient, said method comprising administering to said patient an effective amount of a tricyclic δ opioid receptor agonist of the formula (Ib):

(Ib)

wherein:

X is F, Cl, Br, or I;

$R_1$ is C, N, O or S; and $R_3$ is $-H$ or $-CH_3$.

(Ic)

wherein R is $-H$ or methyl.

4. A method of inducing analgesia in a patient, said method comprising administering to said patient an effective amount of a compound selected from the group consisting of N-desmethylclozapine, amoxapine, and mixtures thereof.

5. A method of inducing analgesia in a patient, said method comprising administering to said patient an effective amount of a tricyclic δ opioid receptor agonist of the formula (II):

(II)

wherein:

$R_4$ and $R_5$ are independently selected from alkyl, halo, haloalkyl, thio or alkoxy;

$R_6$ is C, N, O or S;

$R_7$ is C or N; and $R_8$ is $-H$ or $-CH_3$.

* * * * *